United States Patent [19]

Lawson et al.

[11] Patent Number: 4,761,483

[45] Date of Patent: Aug. 2, 1988

[54] CHLORO-SUBSTITUTED KETONE IMIDAZOLE DERIVATIVES

[75] Inventors: Kevin R. Lawson; Roger M. Upton, both of High Wycombe, United Kingdom

[73] Assignee: G. D. Searle & Co., Chicago, Ill.

[21] Appl. No.: 748,890

[22] Filed: Jun. 26, 1985

[51] Int. Cl.$^4$ ............................................. C07D 233/64
[52] U.S. Cl. .................... 548/344; 546/278; 548/341; 548/342
[58] Field of Search .................. 548/341, 342, 344; 546/278

[56] References Cited

U.S. PATENT DOCUMENTS

| | | | |
|---|---|---|---|
| 4,107,314 | 8/1979 | Cox et al. | 548/341 |
| 4,144,346 | 3/1979 | Heeres et al. | 548/336 |
| 4,223,036 | 9/1980 | Heeres et al. | 548/262 |
| 4,377,697 | 3/1983 | Fellner et al. | 548/336 |

FOREIGN PATENT DOCUMENTS

| | | | |
|---|---|---|---|
| 117578 | 9/1984 | European Pat. Off. | 548/341 |
| 2067993 | 8/1981 | United Kingdom | 548/341 |

OTHER PUBLICATIONS

Sawyer, P. et al., *Drugs,* 1975, 9, 406–423.

*Primary Examiner*—Richard A. Schwartz
*Attorney, Agent, or Firm*—Richard E. L. Henderson; Paul D. Matukaitis

[57] ABSTRACT

The present invention relates to a class of novel chloro-substituted ketone imidazole derivatives. The invention further relates to pharmaceutical compositions containing such compounds and to the use of such compounds and compositions as anti-anaerobic agents.

8 Claims, No Drawings

CHLORO-SUBSTITUTED KETONE IMIDAZOLE DERIVATIVES

BACKGROUND OF THE INVENTION

The present invention relates to a class of novel chlorosubstituted ketone imidazole derivatives. The invention further relates to pharmaceutical compositions containing such compounds and to the use of such compounds and compositions as anti-anaerobic agents.

Various azole derivatives are useful as anti-fungal agents. U.S. Pat. No. 4,107,314 describes a class of heterocyclic thioalkyl substituted imidazole derivatives useful as anti-anaerobic agents. U.S. Pat. Nos. 4,144,346 and 4,223,036 describe a class of 1-(1,3-dioxolan-2-ylmethyl)-1H-imidazoles and 1-(1,3-dioxolan-2-ylmethyl)-1H-1,2,4-triazoles respectively, which are useful as antifungal and anti-bacterial agents. Miconazole, described by P. R. Sawyer, R. N. Brogden, R. M. Pinder, T. M. Speight and G. S. Avery, *Drugs,* 1975, 9, 406, is a topical and intravenous anti-fungal agent. European Patent Application No. 117578 describes a class of azole-substituted alcohol derivatives. UK Pat. No. 2067993 describes a class of imidazole hydrazone derivatives useful as anti-anaerobic agents. U.S. Pat. No. 4,377,697 describes a class of imidazole hydrazone and hydrazine derivatives useful as anti-anaerobic and anti-fungal agents. In addition, copending U.S. application, now U.S. Pat. No. 4,628,104, entitled Imidazole Ketone Derivatives and U.S. application Ser. No. 06/717,981 entitled Substituted Alkyl Imidazole Derivatives, both assigned to a common assignee, relate to a class of imidazole ketone derivatives and substituted alkyl imidazole derivatives respectively, which are useful as anti-anaerobic agents such as in the treatment of peridontal diseases.

SUMMARY OF THE INVENTION

This disclosure relates to a class of novel compounds of the formula:

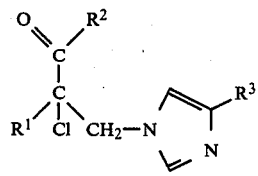

(I)

wherein
$R^1$ is $C_1$–$C_4$ alkyl, phenyl or $C_1$–$C_4$ alkylphenyl;
$R^2$ is $C_1$–$C_7$ alkyl, benzyl, pyridyl, phenyl, halophenyl or dihalophenyl; and
$R^3$ is hydrogen, a

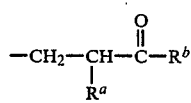

group or a

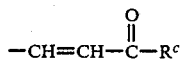

group wherein $R^a$ is hydrogen, amino or a

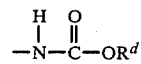

group wherein $R^d$ is benzyl or $C_1$–$C_4$ alkyl; $R^b$ is —$OR^e$ or a

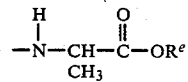

group wherein $R^e$ is hydrogen or $C_1$–$C_4$ alkyl; and $R^c$ is hydroxyl or a

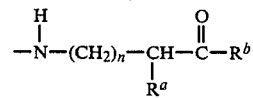

group wherein n is an integer of from 1 to 6 and $R^a$ and $R^b$ are herein defined;
and pharmaceutically acceptable acid addition salts thereof.

This invention further relates to pharmaceutical compositions containing the compounds of formula (I) and to the use of such compounds and compositions as anti-anaerobic agents, such as in the treatment of peridontal disease.

DETAILED DESCRIPTION OF THE INVENTION

The "$C_1$–$C_4$ alkyl" and "$C_1$–$C_7$ alkyl" groups specified herein include straight chain or branched chain hydrocarbon radicals having from one to four and from one to seven carbon atoms respectively. Illustrative of such $C_1$–$C_4$ alkyl radicals include methyl, ethyl, propyl, isopropyl, butyl, isobutyl, sec-butyl and tert-butyl. Illustrative of such $C_1$–$C_7$ alkyl radicals include methyl, ethyl, propyl, isopropyl, butyl, isobutyl, sec-butyl, tert-butyl, pentyl, neopentyl, hexyl, heptyl, and the like.

As used herein the terms "halogen" or "halo" refer to fluoro, chloro, bromo and iodo.

As used herein the terms "halophenyl" and "dihalophenyl" refer to a phenyl radical substituted with one or two halogen substituents respectively. Representative of halophenyl moieties includes fluorophenyl, chlorophenyl, iodophenyl and bromophenyl. It is preferred that the halogen substituent be in the 2- or 4- position of the phenyl radical. Representative of dihalophenyl moieties include difluorophenyl, dichlorophenyl, dibromophenyl, chlorobromophenyl, fluorochlorophenyl, iodobromophenyl and the like. It is preferred that the halogen substituents be in the 2,4- or 3,5- positions of the phenyl radical.

The compounds of the present invention may be prepared in accordance with the following procedure:
An alcohol of the formula

(II)

wherein $R^1$ and $R^2$ are above defined; is reacted with barium manganate at reflux temperatures in an appropriate solvent or alternatively a mixture of oxalyl chloride and dimethylsulfoxide at a temperature of about −70° C., to yield a substituted ketone of the formula:

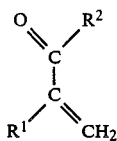
(III)

The substituted ketone of formula (III) is reacted with imidazole or a substituted imidazole to yield a compound of the formula

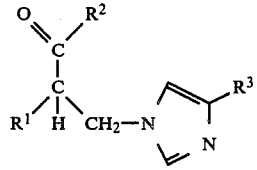
(IV)

wherein $R^3$ is above defined.

The compounds of formula (I) may be produced by reacting a compound of formula (IV) with copper-II-chloride at a temperature of about 80° C. in an appropriate solvent. Alternatively a compound of formula (IV) is reacted with a base such as lithium hexamethyldisilazide in an appropriate solvent, followed by reaction with N-chlorosuccinimide at a temperature of about −70° C., to yield a compound of formula (I).

The alcohols of formula (II) utilized as starting materials may be prepared by reacting a 1-halo-1-substituted ethene of the formula

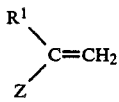
(V)

wherein $R^1$ is above defined and Z is halogen; with magnesium under reflux conditions in an appropriate solvent to yield a magnesium halide of the formula

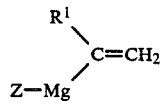
(VI)

The magnesium halide of formula (VI) is reacted with a substituted aldehyde of the formula

(VII)

to yield the alcohol of formula (II).

Alternatively, a substituted ethanone of the formula

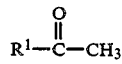
(VIII)

wherein $R^1$ is above defined is reacted with a substituted phenylsulfonylhydrazine in an appropriate solvent to yield a substituted hydrazone derivative of the formula

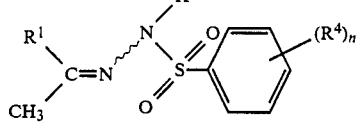
(IX)

wherein $R^4$ is $C_1$–$C_4$ alkyl and n is an integer of from 0 to 3. An alkyl lithium is added to the reaction mixture at a temperature less than −60° C., followed by the addition of a substituted aldehyde of the formula

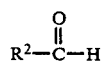
(X)

to yield the alcohol of the formula (II).

The temperatures at which the above reactions are conducted are not critical. It is preferred to conduct the above reactions at a temperature sufficient to allow the reactions to proceed towards completion. Such temperatures vary from reaction to reaction and are readily ascertained by one of ordinary skill in the art.

The appropriate solvents employed in the above reactions are solvents wherein the reactants are soluble but do not react with the reactants. The preferred solvents vary from reaction to reaction and are readily ascertained by one of ordinary skill in the art.

The compounds of formula (I) form acid addition salts with an appropriate acid such as hydrohalogenic acid (e.g., hydrochloric acid, hydrobromic acid), sulfuric acid, phosphoric acid, succinic acid, glycolic acid, lactic acid, gluconic acid, tartaric acid, citric acid, maleic acid, malic acid, fumaric acid, methanesulfonic acid, p-toluenesulfonic acid, oxalic acid, ascorbic acid, benzoic acid, trifluoroacetic acid or the like. The pharmaceutically acceptable acid addition salts are preferred.

The pharmaceutically acceptable salts of the compounds of the present invention may be prepared by conventional procedures, e.g., by reacting the free base in a suitable solvent, e.g., diethyl ether or ethanol, with a solution containing one equivalent of the desired acid in a suitable solvent, e.g., diethyl ether or ethanol. The salt generally precipitates from solution or is recovered by evaporation of the solvent.

The preferred embodiment of the present invention includes compounds of formula (I) wherein $R^1$ is phenyl, $R^2$ is halophenyl or dihalophenyl, and $R^3$ is a

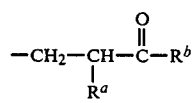

group or a

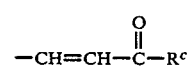

group wherein $R^a$ is hydrogen, amino or a

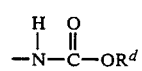

group wherein $R^d$ is benzyl or $C_1$-$C_4$ alkyl, $R^b$ is $-OR^e$ or a

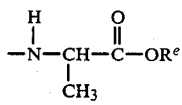

group wherein $R^e$ is hydrogen or $C_1$-$C_4$ alkyl, and $R^c$ is hydroxyl or a

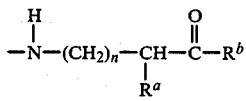

group wherein n is an integer of from 1 to 6 and $R^a$ and $R^b$ are herein defined. Suitably $R^3$ is

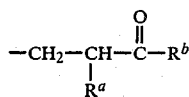

and $R^1$ and $R^2$ are as defined in said preferred embodiment. A more preferred embodiment of the present invention includes compounds of formula (I) wherein $R^1$ is phenyl, $R^2$ is dihalophenyl, and $R^3$ is a

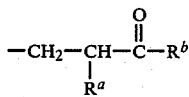

group wherein $R^a$ is hydrogen, amino or a

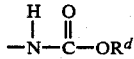

group wherein $R^d$ is hydrogen or $C_1$-$C_4$ alkyl, $R^b$ is $-OR^e$ or a

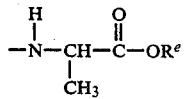

wherein $R^e$ is herein defined. A most preferred embodiment of the present invention includes compounds of formula (I) wherein $R^1$ is phenyl, $R^2$ is dichlorophenyl and $R^3$ is a

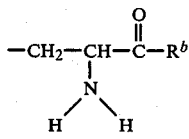

group wherein $R^b$ is $-OR^e$ or

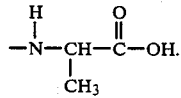

The compounds of the present invention may be administered topically, preferably in the form of a pharmaceutical composition adapted to such a route, and in a dose effective for the treatment intended. Therapeutically effective doses of the compounds of the present invention are readily ascertained by one of ordinary skill in the art.

Accordingly, the invention provides a class of novel pharmaceutical compositions comprising one or more compounds of the present invention in association with one or more non-toxic, pharmaceutically acceptable carriers and/or diluents and/or adjuvants and if desired other active ingredients.

Representative carriers, diluents and adjuvants include for example water, lactose, gelatin, starches, magnesium stearate, talc, vegetable oils, gums, polyalkylene glycols, petroleum jelly, etc. The pharmaceutical compositions may be made up in a solid form such as granules, powders or suppositories or in a liquid form such as solutions, suspensions or emulsions. The pharmaceutical compositions may be subjected to conventional pharmaceutical operations such as sterilization and/or may contain conventional pharmaceutical adjuvants such as preservatives, stabilizers, wetting agents, emulsifiers, buffers, etc.

As indicated, the dose administered and the treatment regimen will be dependent, for example, on the disease, the severity thereof, on the patient being treated and his response to treatment and therefore may be widely varied.

The following Examples are intended to further illustrate the present invention and not to limit the invention in spirit or scope. In the Examples, all parts are parts by weight unless otherwise expressly set forth.

EXAMPLE 1

1-(2,4-Dichlorophenyl)-2-phenylpropen-1-one

A mixture of magnesium metal (0.73 g) and 1-bromo-1-phenylethene (4.9 g) in tetrahydrofuran (75ml) was heated at reflux. To the reaction mixure was added a solution of 2,4-dichlorobenzaldehyde (4.7 g) in tetrahydrofuran (25 ml) and the resulting mixture was maintained at reflux for 4 hours. The reaction mixture was cooled and poured into dilute hydrochloric acid. The resulting mixture was extracted with ethyl acetate and the organic phase was washed with water, dried over anhydrous magnesium sulfate and concentrated under reduced pressure to yield a gum (7 g), which was chromatographed on silica gel eluting with a mixture of ethyl acetate: hexane (1:1) to yield α-(1-phenylethenyl)-2,4-dichlorobenzenemethanol (5 g).

To a solution of α-(1-phenylethenyl)-2,4-dichlorobenzenemethanol (4 g) in toluene (100 ml) was added barium manganate (5 g) and the resulting mixture heated at reflux under an atmosphere of nitrogen for a period of 12 hours. The reaction mixture was cooled, filtered and concentrated under reduced pressure to yield 1-(2,4-dichlorophenyl)-2-phenylpropen-1-one, (δ (CDCl$_3$), 5.75 (1H,s), 6.3 (1H,s) and 7.25-7.60 (8H,m)) as a gum (4.3 g) having the formula:

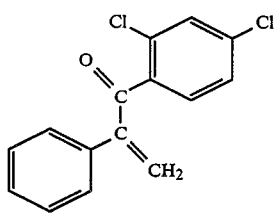

EXAMPLE 2

1-(2,4-Dichlorophenyl)-3-(imidazol-1-yl)-2-phenylpropan-1-one

A solution of 1-(2,4-dichlorophenyl)-2-phenylpropen-1-one (4g), imidazol (1.36 g) and tetramethylquanidine (0.5 ml) in tetrahydrofuran (100 ml) was heated at reflux for 12 hours. The reaction mixture was cooled and concentrated under reduced pressure to yield a gum. The gum was dissolved in ethyl acetate, washed with distilled water, and acidified with 4N hydrochloric acid. The aqueous phase was basified with sodium carbonate and extracted with ethyl acetate. The organic phase was separated, washed with distilled water, dried over anhydrous magnesium sulphate and concentrated under reduced pressure to yield an oil which was chromatographed on silica gel using a mixture of methanol/dichloromethane (1:9) as an eluent to yield 1-(2,4-dichlorophenyl)-3-(imidazol-1-yl)-2-phenylpropan-1-one (600 mg), which was treated with ethereal hydrogen chloride to yield the hydrochloride salt of 1-(2,4-dichlorophenyl)-3-(imidazol-1-yl)-2-phenylpropan-1-one, m.p. 110° C., (Found: C, 55.38; H, 4.37; N, 7.40%; $C_{18}H_{15}Cl_3N_2O.\frac{1}{2}H_2O$ requires C, 55.34; H, 4.13; N, 7.17%) having the formula:

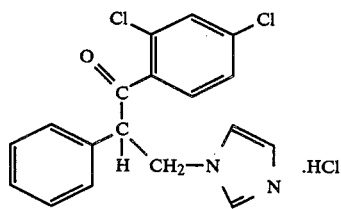

EXAMPLE 3

E-3-[1-[3-(2,4-Dichlorophenyl)-3-oxo-2-phenylpropyl-]imidazol-4-yl]propenoic acid A solution of E-3-(imidazol-4-yl)propenoic acid (8 g) in hot dimethylformamide (100 ml) was cooled until crystallization commenced. To the reaction mixture was rapidly added a solution of 1-(2,4-dichlorophenyl)-2-phenylpropen-1-one (4 g) in ethanol (8 ml). The resulting mixture was cooled to 20° C. Ethyl acetate was added to the mixture and the resulting mixture was washed with water, dried over anhydrous magnesium sulphate and concentrated under reduced pressure to yield a white solid which was repeatedly washed with hexane.

Recrystallization of the white solid from ethyl acetate:hexane (1:1) yielded white crystals of E-3-[1-[3-(2,4-dichlorophenyl)-3-oxo-2-phenylpropyl]imidazol-4-yl]propenoic acid (4 g), m.p. 229–231° C., (Found: C, 59.86; H, 3.81; N, 6.60%; $C_{21}H_{16}N_2Cl_2O_3.\frac{1}{2}H_2O$ requires C, 59.45; H, 4.03; N, 6.60%) having the formula:

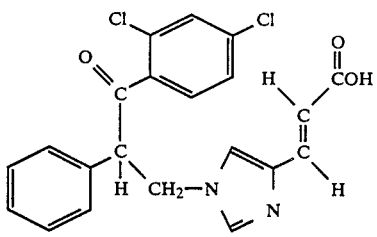

EXAMPLE 4

2-Chloro-1-(2,4-dichlorophenyl)-3-(imidazol-1-yl)-2-phenylpropan-1-one

To a stirred solution of lithium hexamethyldisilazide (5.5 ml, 1M in tetrahydrofuran) in dry tetrahydrofuran (20 ml) at −78° C., under an atmosphere of nitrogen, was added dropwise a solution of 1-(2,4-dichlorophenyl)-3-(imidazol-1-yl)-2-phenylpropen-1-one (1.725 g) in dry tetrahydrofuran (5 ml). The resulting mixture was stirred for 30 minutes and then a solution of N-chlorosuccinimide (810 mg) in dry hexamethylphosphoramide (8 ml) was added to the mixture. The mixture was allowed to warm to 20° C. and saturated aqueous ammonium chloride was added. The organic phase was removed and the aqueous phase extracted with ethyl acetate. The organic extracts were combined, washed with brine, dried over anhydrous magnesium sulphate and concentrated under reduced pressure to yield an oil (2.2 g). The oil was chromatographed on silica gel eluting with a mixture of methanol:dichloromethane (1:99) to yield 2-chloro-1-(2,4-dichlorophenyl)-3-(imidazol-1-yl)-2-phenylpropan-1-one as an oil which, upon treatment with ethereal hydrogen chloride yielded the hydrochloride salt of 2-chloro-1-(2,4-dichlorophenyl)-3-(imidazol-1-yl)-2-phenylpropan-1-one as a hygroscopic solid (1.5 g), (Found: C, 50.59; H, 3.52; N, 6.50%; $C_{18}H_{14}Cl_4N_2O.\frac{1}{2}H_2O$ requires C, 50.85; H; 3.56; N, 6.59%), having the formula:

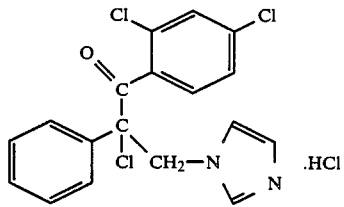

FORMULA 5

3-[1-[2-Chloro-3-(2,4-dichlorophenyl)-3-oxo-2-phenylpropyl]-imidazol-4-yl]propanoic acid methyl ester 3-(Imidazol-4-yl)propanoic acid methyl ester (4 g) was added to a solution of 1-(2,4-dichlorophenyl)-2-phenylpropen-1one (7.5 g) in ethanol (50 ml) and the resulting solution maintained at 20° C. for 12 hours. The solvent was removed under reduced pressure to yield 3-[1-[3-(2,4-dichlorophenyl)-3-oxo-2-phenylpropyl]imidazol-4-yl]propanoic acid methyl ester (12 g) as an oil. A portion of the oil (3 g) was dissolved in dimethylformamide (50 ml) and copper-II-chloride dihydrate (10 g) added to the solution. The resulting solution was heated at 80° C. for 18 hours and then cooled to room temperature. Water was added to the reaction mixture and the aqueous phase extracted twice with ethyl acetate. The organic phases were combined, washed with dilute aqueous ammonia, water, and brine, dried over anhydrous magnesium sulphate and concentrated under reduced pressure to yield a gum (2.75 g). The gum was chromatographed on silica gel eluting with a mixture of methanol:dichloromethane (1.5:98.5) to yield an oil upon treatment with ethereal hydrogen chloride yielded the hydrochloride salt of 3-[1-[2-chloro-3-(2,4-dichlorophenyl)-3-oxo-2-phenylpropyl]imidazol-4-yl]propanoic acid methyl ester (1.56 g), m.p. 144–7° C., (Found: C, 52.75; H, 4.13; N, 5.57%; $C_{22}H_{20}Cl_4N_2O_3$ requires C, 52.61; H, 4.01; N, 5.58%), having the formula:

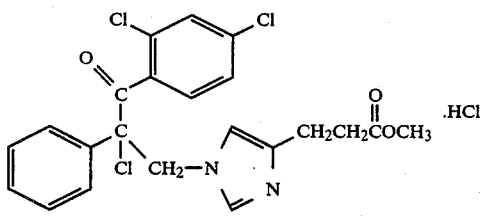

EXAMPLE 6

E-3-[1-[2-Chloro-3-(2,4-dichlorophenyl)-3-oxo-2-phenylpropyl]imidazol-1-yl]propenoic acid hydrochloride A mixture of E-3-[1-[3-(2,4-dichlorophenyl)-3-oxo-2-phenylpropyl]imidazol-4-yl]propenoic acid (1 g) and copper-II-chloride dihydrate (5 g) in dimethylformamide (50 ml) was heated at 80° C. for 18 hours. The mixture was cooled to 20° C. and water was added and the resulting mixture extracted with ethyl acetate. The organic phase was washed repeatedly with water, then washed with brine, dried over anhydrous magnesium sulphate and concentrated under reduced pressure to yield a crude product (800 mg) as a foam. The crude product was purified by chromatography on silica gel using a mixture of methanol:dichloromethane (1:19) as an eluent to yield E-3-[1-[2-chloro-3-(2,4-dichlorophenyl)-3-oxo-2-phenylpropyl]imidazol-1-yl]propenoic acid which was treated with ethereal hydrogen chloride to yield the hydrochloride salt of E-3-[1-[2-chloro-3-(2,4-dichlorophenyl)-3-oxo-2-phenylpropyl]imidazol-1-yl]propenoic acid (430 mg), m.p. 135–145° C., recrystallized from ethanol/ether, (Found: C, 51.70; H, 4.13; N, 5.14%; $C_{21}H_{16}Cl_4N_2O_3.C_2H_5OH$ requires C, 51.90; H, 4.17; N, 5.26%); having the formula:

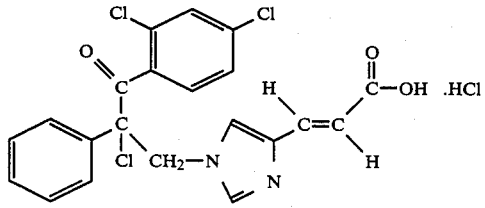

EXANPLE 7

1-[2-Chloro-3-(2,4-dichlorophenyl)-3-oxo-2-phenylpropyl]- N-[(1,1-dimethylethoxy)carbonyl]-L-histidine Water was added to a stirred suspension of N-[(1,1-dimethylethoxy)carbonyl]-L-histidine (13.26 g) in ethanol (100 ml) and 1-(2,4-dichlorophenyl)-2-phenylpropen-1-one (14.5 g) until a clear solution was obtained. The clear solution was allowed to stand for 18 hours, and was then concentrated under reduced pressure to yield a foam which was triturated with hexane. The resulting mixture was filtered to yield 1-[3-(2,4-dichlorophenyl)-3-oxo-2-phenylpropyl]-N-[(1,1-dimethylethoxy)carbonyl]-L-histidine (27.7 g), as a mixture of diastereoisomers.

A portion of the 1-[3-(2,4-dichlorophenyl)-3-oxo-2-phenylpropyl]-N-[(1,1-dimethylethoxy)carbonyl]-L-histidine (5.5 g) in dry tetrahydrofuran (50 ml) was added dropwise to a stirred solution of lithium hexamethyldisilazide in tetrahydrofuran (33 ml, 1M solution in tetrahydrofuran) at −78° C. under an atmosphere of nitrogen. After 30 minutes the resulting solution was rapidly transferred, under an atmosphere of nitrogen, into a stirred solution of N-chlorosuccinimide (1.6 g) in dry tetrahydrofuran (50 ml). The resulting mixture was cooled in an ice bath under an atmosphere of nitrogen. The mixture was allowed to warm to room temperature over a period of 20 minutes and was quenched upon an addition of an excess of saturated aqueous potassium dihydrogen orthophosphate. The organic phase was separated and the aqueous phase was extracted twice with ethyl acetate. The organic phases were combined, dried over anhydrous magnesium sulphate and concentrated under reduced pressure to yield a residue. The residue was dissolved in ethyl acetate, washed with water and then brine, dried over anhydrous magnesium sulphate and concentrated under reduced pressure to yield a foam which was chromatographed on silica gel using a mixture of methanol:dichloromethane (2:23) as an eluent to yield 1-[2-chloro-3-(2,4-dichlorophenyl)-3-oxo-2-phenylpropyl]-N-[(1,1-dimethylethoxy)carbonyl]-L-histidine (2.85 g) as a mixture of diastereoisomers, (δ (CDCl₃) 1.45 (9H, s), 1.48 (9H, s), 3.01 (2H, bd, J=15Hz), 3.23 (2H, bd, J=15Hz), 4.35 (2H, bs), 4.62 (2H, bt, J=17Hz), 4.86 (2H, bt, J=17Hz), 5.48 (2H, m, 4 lines), 6.38 (1H, bs), 6.57 (3H, m), 6.98 (2H, dd, J=9Hz and 2Hz), 7.42 (2H, m), 7.46 (5H, s), 7.49 (5H, s), 7.56 (1H, bs) and 7.60 (1H, bs)), having the formula:

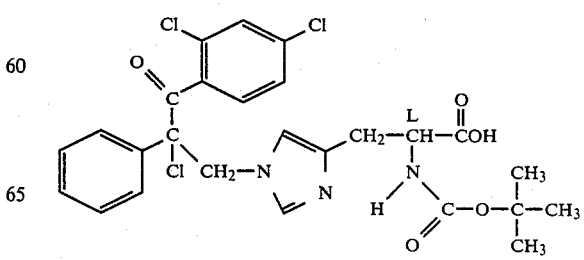

EXAMPLE 8

1-[2-Chloro-3-(2,4-dichlorophenyl)-3-oxo-2-phenylpropyl]-L-histidine

A solution of 1-[2-chloro-3-(2,4-dichlorophenyl)-3-oxo-2-phenylpropyl]-N-[(1,1-dimethylethoxy)carbonyl]-L-histidine (330 mg) in 98% formic acid (10 ml) was allowed to stand for 16 hours. The solution was concentrated under reduced pressure and triturated with ether to yield a solid product which was dissolved in dichloromethane. Ethereal hydrogen chloride was added to the dichloromethane solution and subsequent addition of diethyl ether yielded the dihydrochloride salt of 1-[2-chloro-3-(2,4-dichlorophenyl)-3-oxo-2-phenylpropyl]-L-histidine as a buff coloured powder (220 mg), as a mixture of diastereoisomers, m.p. 185–190° C. (decomp), (Found: C, 46.72; H, 3.85; N, 7.92%; $C_{21}H_{20}Cl_5N_3O_3$ requires C, 46.74; H, 3.74; N, 7.79%) having the formula:

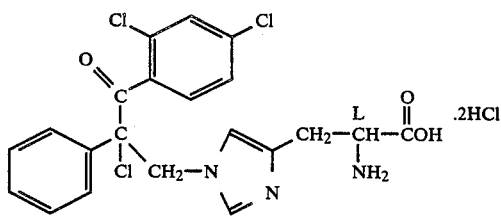

EXAMPLE 9

N-[1-[2-Chloro-3-(2,4-dichlorophenyl)-3-oxo-2-phenylpropyl]-N-[(1,1-dimethylethoxy)carbonyl]-L-histidyl]-L-alanine 1,1-dimethylethyl ester To a stirred mixture of 1-[2-chloro-3-(2,4-dichlorophenyl)-3-oxo-2-phenylpropyl]-N-[(1,1-dimethylethoxy)carbonyl]-L-histidine (1.14 g), N-methylmorpholine (461 μl), 1-hydroxybenzotriazole hydrate (277 mg) and L-alanine 1,1-dimethylethyl ester hydrochloride (364 mg) in dichloromethane (30 ml) was added N-(3-dimethylaminopropyl)-N'-ethylcarbodiimide hydrochloride (422 mg). The resulting mixture was stirred for 18 hours, and concentrated under reduced pressure to yield a residue which was partitioned between ethyl acetate and water. The organic phase was washed with saturated aqueous sodium hydrogen carbonate and then brine and dried over anhydrous magnesium sulphate. The solvent was removed under reduced pressure to yield a foam which was chromatographed on silica gel eluting with methanol/dichloromethane (1:24) to yield N-[1-[2-chloro-3-(2,4-dichlorophenyl)-3-oxo-2-phenylpropyl]-N-[(1,1-dimethylethoxy)carbonyl]-L-histidyl]-L-alanine 1,1-dimethylethyl ester as a white foam (1.25 g), and as a mixture of diastereoisomers, m.p. 85–90° C. (decomp), (Found: C, 55.57; H, 5.51; N, 7.86%; $C_{33}H_{39}Cl_3N_4O_6.H_2O$ requires C, 55.66; H, 5.80; N, 7.87%), having the formula:

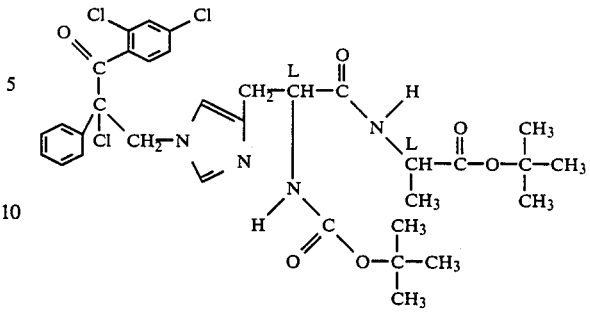

EXAMPLE 10

N-[1-[2-Chloro-3-(2,4-dichlorophenyl)-3-oxo-2-phenylpropyl]-L-histidyl]-L-alanine N-[1-[2-Chloro-3-(2,4-dichlorophenyl)-3-oxo-2-phenylpropyl]-N-[(1,1-dimethylethoxy)carbonyl]-L-histidyl]-L-alanine 1,1-dimethylethyl ester (800 mg) was treated with trifluoroacetic acid (5 ml) and the resulting solution was allowed to stand for 18 hours. The solution was concentrated under reduced pressure to yield a gum which was dissolved in dichloromethane and treated with ethereal hydrogen chloride to yield the dihydrochloride salt of N-[1-[2-chloro-3-(2,4-dichlorophenyl)-3-oxo-2-phenylpropyl]-L-histidyl]-L-alanine (640 ml) as a mixture of diastereoisomers, m.p. 154–156° C., (Found: C, 46.26; H, 4.04; N, 8.85%; $C_{24}H_{25}Cl_5N_4O_4$.

0.75 $H_2O$ requires C, 46.24; H, 4.27; N, 8.99%) having the formula:

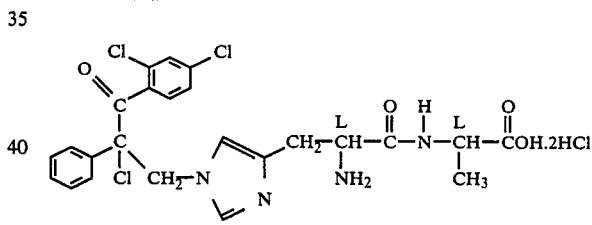

EXAMPLE 11

N-[$N^6$-[E-3-[1-[2-Chloro-3-(2,4-dichlorophenyl)-3-oxo-2-phenylpropyl]imidazol-4-yl]propenyl]-$N^2$-[(1,1-dinethylethoxy)carbonyl]-L-lysinyl]-L-alanine-1,1-dimethylethyl ester N-Methylmorpholine (3.3 ml) was added to a suspension of L-alanine 1,1-dimethylethyl ester (4.0 g), $N^2$-[(1,1-dimethylethoxy)carbonyl]-$N^6$-[(phenylmethoxy)carbonyl]-L-lysine (11.4 g), N-(3-dimethylaminopropyl)-N'-ethylcarbodiimide hydrochloride (5.8 g) and 1-hydroxybenzotriazole (4.1 g) in dichloromethane (150 ml). The resulting mixture was allowed to stand for 18 hours, and was then poured into distilled water (200 ml). The organic phase was separated, washed with water, saturated sodium hydrogen carbonate, dilute aqueous citric acid, brine and dried over anhydrous magnesium sulphate. The solvent was removed under reduced pressure to yield N-[$N^2$-[(1,1-dimethylethoxy)carbonyl]-$N^6$-[(phenylmethoxy)carbonyl]-L-lysinyl]-L-alanine 1,1-dimethylethyl ester (12.6 g) as a foam.

A mixture containing a portion of the N-[$N^2$-[(1,1-dimethylethoxy)carbonyl]-$N^6$-[(phenylmethoxy)carbonyl]-L-lysinyl]-L-alanine 1,1-dimethylethyl ester (6 g) and glacial acetic acid (0.66 ml) in methanol (60 ml) was hydrogenated over 10% palladium on carbon (2.4 g). The mixture was filtered through Celite, and the solvent was removed under reduced pressure to yield the acetate salt of N-[N$^2$-[(1,1-dimethylethoxy)carbonyl]-L-lysinyl-9 - L-alanine 1,1-dimethylethyl ester (4.6 g) as a hygroscopic foam.

N-Methylmorpholine (800 μl) was added to a suspension containing E-3-[1-[2-chloro-3-(2,4-dichlorophenyl)-3-oxo- 2-phenylpropyl]imidazol-1-yl]propenoic acid hydrochloride (1.1 g), the acetate salt of (N-[N-$^2$-[(1,1- dimethylethoxy)carbonyl]-L-lysinyl]-L-alanine 1,1-dimethylethyl ester (14) (1.1 g), N-(3-dimethylaminopropyl)-N'-ethylcarbodiimide hydrochloride (0.46 g) and 1-hydroxybenzotriazole (0.32 g) in dichloromethane (60 ml). The resulting mixture was allowed to stand for 18 hours, and was then poured into water and the organic phase was separated. The organic phase was washed with water, saturated aqueous sodium hydrogen carbonate, dilute aqueous citric acid, brine and dried over anhydrous magnesium silphate. The solvent was removed under reduced pressure to yield N-[N$^6$-[E-3-[1-[2-chloro-3-(2,4-dichlorophenyl)-3-oxo-2- phenylpropyl]imidazol-4-yl]propenoyl]-N$^2$-[(1,1- dimethylethoxy)carbonyl]-L-lysinyl]-L-alanine 1,1-dimethylethyl ester (800 mg) as a hygroscopic foam, as a mixture of diastereiosomers, (δ (CDCl$_3$) 1.34 (3H, d, J-6Hz), 1.43 (9H, s), 1.46 (9H, s), 3.20–3.40 (2H, m), 4.10 (1H, m), 4.42 (1H, dt, J=14Hz and 7Hz), 4.70 (1H, d, J=15Hz), 4.90 (1H, d, J=15Hz), 5.30 (1H, m), 5.94 (1H, m), 6.52 (1H, d, J=15Hz), 6.58 (1H, d, J=8Hz), 6.74 (1H, s), 6.84 (1H, m), 6.98 (1H, dd, J=8Hz and 1Hz), 7.28 (1H, s), 7.31 (1H, d, J=15Hz), 7.42 (1H, d, J=1Hz) and 7.48 (5H, m)) having the formula:

EXAMPLE 12

N-[N$^6$-[E-3-[1-[2-Chloro-3-(2,4-dichlorophenyl)-3-oxo-2-phenylpropyl]imidazol-4-yl]propenoyl]-L-lysinyl]-L-alanine N-[N$^6$-[E-3-[1-[2Chloro-3-(2,4-dichlorophenyl)-3-oxo-2- phenylpropyl]imidazol-4-yl]propenoyl]-N$^2$-[(1,1- dimethylethoxy)carbonyl-L-lysinyl]-L-alanine 1,1 dimethylethyl ester (500 mg.) was dissolved in trifluoroacetic acid (5 ml). The resulting solution was allowed to stand for 18 hours after which the solvent was removed under reduced pressure, and the resulting residue was triturated with diethyl ether to yield a white solid which was purified by reverse phase chromatography on octadecylsilylated silica gel using methanol:water (60:40–70:30) as an eluent, to yield the bistrifluoroacetate salt of N-[N$^6$-[E-3-[1-[2-chloro- 3-(2,4-dichlorophenyl)-3-oxo-2-phenylpropyl]imidazol-4- yl]propenoyl]-L-lysinyl]-L-alanine (220 mg), as a mixture of diastereoisomers, m.p. 124–127° C., (Found: C, 46.56; H, 4.12; N, 8.11%: C$_{34}$H$_{34}$Cl$_3$F$_6$N$_5$O$_9$ requires C, 46.56; H, 3.91; N, 7.99%) having the formula:

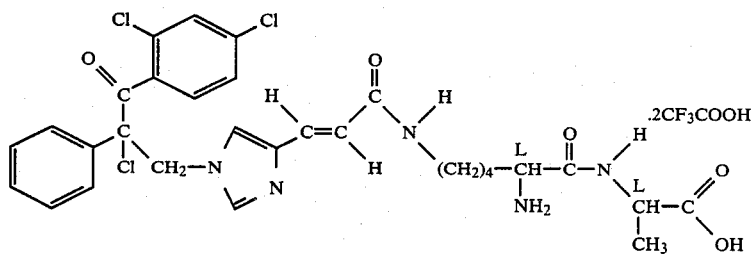

The anti-anaerobic activity of the compounds of the present invention is illustrated by the following Examples.

EXAMPLE 13

The screening panel utilized in the Example consisted of 5 strains of *Bacteroides fragilis.* All assays were carried out in 96 well microtitre plates. If an isolate was obtained from either a culture collection or clinical source, the isolate was immediately innoculated into Wilkens-Chalgren broth (Oxoid) and incubated at 37° C. in an anaerobic chamber in an atmosphere of 85% nitrogen, 10% carbon dioxide, and 5% hydrogen for 48 hours. At the end of this time, the viable count was about 10$^{12}$ organisms/ml broth. A 1 ml aliquot of each culture was placed in an ampoule and quick frozen in acetone-dry ice mixture and stored in liquid nitrogen. When an

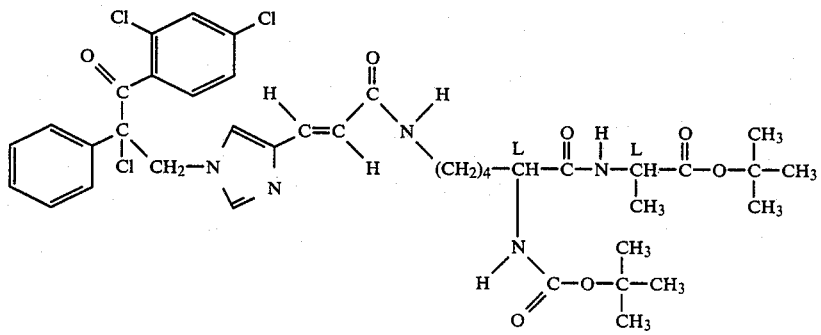

inoculum was utilized in an assay, one of the ampoules was thawed and diluted with fresh broth to yield a suspension having a count of $5 \times 10^5$ organisms/ml. A 100 μl aliquot of the suspension was inoculated into each well of the microtitre plate.

A 2 mg sample of the test compound wa dissolved in 0.2 ml of a suitable solvent such as dimethylsulfoxide, polyethylene glycol 200 or methanol. The solution was then diluted with 4.8 ml of water to yield a solution having a concentration of 400 mg/L. Doubling dilutions of this stock were prepared to give a range of concentrations from 1.6–200 mg/L. 100 μl of each concentration were then placed in the wells of the microtitre plate containing the inoculum, to produce a final concentration range of 0.8–100 mg/l. Metronidazole was employed as a positive control and a solvent/water mixture was employed as a negative control. After addition of the test solution the final inoculum level was $10^5$ cells/ml. The plates were incubated for 48 hours at 37° C. in the anaerobic chamber. The Minimum Inhibitory Concentration (MIC) was read visually. The MIC is defined as the lowest concentration at which there is no detectable growth. The Minimum Bactericidal Concentration (MBC) was determined by taking a 50 μl aliquot from each well and placing it in fresh medium. The MBC is defined as the lowest concentration at which there is less than 5 colonies (i.e., 99.9% reduction in viable count) after 48 hours of incubation. The MIC and MBC values for each compound tested and the respective MIC and MBC value for metronidazole are indicated in Table I. The MIC and MBC value for the negative control that was assayed along with each test compound was greater than 100 mg/L. The MIC and MBC values in Table I are expressed in mg/L. A blank in the table represented by a "—" indicates that the assay was not conducted using the strain indicated.

The strains of *Bacteroides fragilis* utilized in the above procedure are identified by letter in accordance with the following legend:

| STRAIN | ORGANISM |
|---|---|
| A | B. fragilis NCTC 10581 |
| B | B. fragilis NCTC 9343 |
| C | B. fragilis NCTC 9344 |
| D | B. fragilis MZ-R ATCC 11295 |
| E | B. fragilis WS-1* |

*Obtained from St. Thomas's Hospital Medical School, London, United Kingdom

EXAMPLE 14:

Conducting the procedures described in Example 13, the anti-anerobic activity of certain compounds of the present invention was demonstrated utilizing an additional 12 strains of various anerobic bacteria.

The MIC values obtained are indicated in Table II. A blank in the table represented by a "—" indicates that the assay was not conducted using the strain indicated.

TABLE II

| STRAIN | COMPOUND OF EXAMPLE 4 MIC | METRONIDAZOLE MIC |
|---|---|---|
| *Clostridium perfringens* NCTC 523 | 0.8 | 0.8 |
| *Clostridium perfringens* NCTC 8237 | 0.8 | 0.8 |
| *Campylobacter fetus* ATCC 29428 | 0.8 | >100 |
| *Fusobacterium necrophorum* ATCC 11295 | 0.8 | 6.2 |
| *Peptococcus magnus* ATCC 29328 | 0.8 | 0.8 |
| *Peptococcus prevotti* ATCC 9321 | 0.8 | 1.5 |
| *Peptostreptococcus anaerobicus* ATCC 27337 | 0.8 | 0.8 |
| *Propionibacterium acnes* NCTC 737 | 0.8 | >100 |
| *Propionibacterium acnes* NCTC 7337 | 0.8 | >100 |

Although this invention has been described with respect to specific modification, the details thereof are not to be construed as limitations, for it will be apparent that various equivalents, changes and modifications may be resorted to without departing from the spirit and scope thereof and it is understood that such equivalent embodiments are intended to be included therein.

What is claimed is:

1. A compound of the formula:

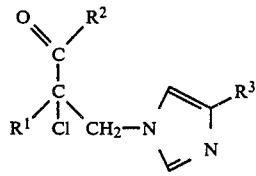

wherein
R[1] is C₁–C₄ alkyl, phenyl or C₁–C₄ alkylphenyl;
R[2] is C₁–C₇ alkyl, benzyl, pyridyl, phenyl, halophenyl or dihalophenyl; and

TABLE I

| COMPOUND OF EXAMPLE NO. | STRAIN | | | | | | | | | |
|---|---|---|---|---|---|---|---|---|---|---|
| | A | | B | | C | | D | | E | |
| | MIC | MBC | MIC | MBC | MIC | MBC | MIC | MBC | MIC | MBC |
| 4 | 0.8 | 6.2 | 0.8 | 6.2 | 0.8 | 12.5 | 0.8 | 3.1 | 0.8 | 6.2 |
| Metronidazole | 0.8 | 0.8 | 0.8 | 0.8 | 0.8 | 0.8 | 6.2 | 6.2 | 1.5 | 1.5 |
| 5 | 1.5 | 1.5 | 1.5 | 1.5 | 1.5 | 1.5 | 0.8 | 0.8 | 3.1 | 3.1 |
| Metronidazole | 0.6 | 1.2 | 1.2 | 1.2 | 0.6 | 0.6 | 10.0 | 10.0 | 1.2 | 1.2 |
| 6 | 0.8 | 0.8 | 1.5 | 3.1 | 0.8 | 0.8 | 0.8 | 0.8 | 3.1 | 3.1 |
| Metronidazole | 0.6 | 1.2 | 1.2 | 1.2 | 1.2 | 1.2 | 10.0 | 10.0 | 1.2 | 1.2 |
| 8 | 0.8 | 0.8 | 0.8 | 0.8 | 0.8 | 0.8 | 0.8 | 0.8 | 3.1 | 3.1 |
| Metronidazole | 0.6 | 0.6 | 0.6 | 1.2 | 1.2 | 1.2 | 10.0 | 10.0 | 0.6 | 1.2 |
| 9 | 3.1 | 6.2 | 3.1 | 3.1 | 6.2 | 6.2 | 0.8 | 0.8 | 12.5 | 12.5 |
| Metronidazole | 0.6 | 1.2 | 1.2 | 1.2 | 0.6 | 0.6 | 10.0 | 10.0 | 1.2 | 1.2 |
| 10 | 3.1 | 3.1 | 3.1 | 3.1 | 3.1 | 6.2 | 0.8 | 0.8 | 6.2 | 6.2 |
| Metronidazole | 0.6 | 1.2 | 1.2 | 1.2 | 0.6 | 0.6 | 10.0 | 10.0 | 1.2 | 1.2 |
| 12 | 1.5 | 3.1 | 1.5 | 1.5 | 3.1 | 3.1 | 0.8 | 0.8 | 6.2 | 6.2 |
| Metronidazole | 0.6 | 0.6 | 1.2 | 1.2 | 0.6 | 1.2 | 10.0 | 10.0 | 1.2 | 1.2 |

$R^3$ is hydrogen, a

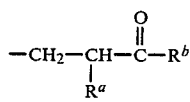

group or a

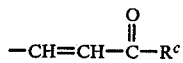

group wherein $R^a$ is hydrogen, amino or a

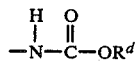

group wherein $R^d$ is benzyl or $C_1$-$C_4$ alkyl; $R^b$ is—$OR^e$ or a

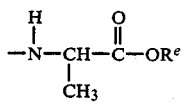

group wherein $R^e$ is hydrogen or

alkyl; and $R^c$ is hydroxyl or a

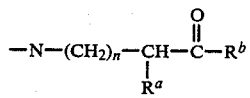

group wherein n is an integer of from 1 to 6 and $R^a$ and $R^b$ are herein defined; or a pharmaceutically acceptable acid addition salt thereof.

2. A compound according to claim 1 wherein $R^1$ is phenyl and $R^2$ is halophenyl or dihalophenyl.

3. A compound according to claim 2 wherein $R^3$ is a

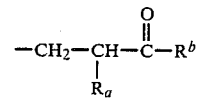

group wherein $R^a$ is hydrogen, amino or a

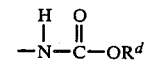

group wherein $R^d$ is benzyl or $C_1$-$C_4$ alkyl, $R^b$ is—$OR^e$ or a

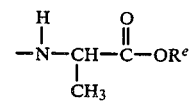

wherein $R^e$ is hydrogen or $C_1$-$C_4$ alkyl.

4. A compound according to claim 3 wherein $R^2$ is dihalophenyl.

5. A compound according to claim 4 wherein $R^a$ is amino and $R^e$ is hydrogen.

6. A compound according to claim 5 wherein $R^2$ is dichlorophenyl.

7. A compound according to claim 6 of the formula

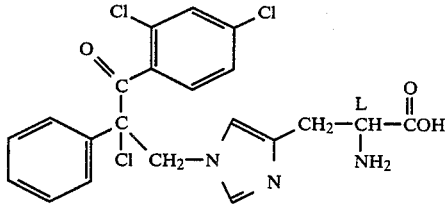

8. A compound according to claim 6 of the formula

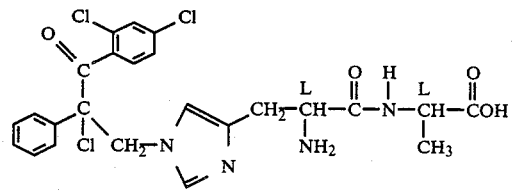

* * * * *

UNITED STATES PATENT AND TRADEMARK OFFICE
CERTIFICATE OF CORRECTION

PATENT NO. : 4,761,483
DATED : August 2, 1988
INVENTOR(S) : Lawson, et. al.

It is certified that error appears in the above-identified patent and that said Letters Patent is hereby corrected as shown below:

Column 7, lines 23-24, reading "sodium carbonate" should read -- sodium hydrogen carbonate --.

Column 13, line 7, reading "-lysinyl-9-L-" should read -- -lysinyl]-L- --.

Signed and Sealed this

Twenty-first Day of May, 1991

Attest:

HARRY F. MANBECK, JR.

Attesting Officer

Commissioner of Patents and Trademarks